US008927211B2

(12) United States Patent
Turner et al.

(10) Patent No.: US 8,927,211 B2
(45) Date of Patent: Jan. 6, 2015

(54) NUCLEOTIDE COMPOSITIONS AND USES THEREOF

(75) Inventors: Stephen Turner, Menlo Park, CA (US); Jonas Korlach, Newark, CA (US)

(73) Assignee: Pacific Biosciences of California, Inc., Menlo Park, CA (US)

( * ) Notice: Subject to any disclaimer, the term of this patent is extended or adjusted under 35 U.S.C. 154(b) by 454 days.

(21) Appl. No.: 12/700,593

(22) Filed: Feb. 4, 2010

(65) Prior Publication Data

US 2010/0240045 A1 Sep. 23, 2010

Related U.S. Application Data

(62) Division of application No. 11/352,170, filed on Feb. 9, 2006, now Pat. No. 7,767,394.

(60) Provisional application No. 60/651,846, filed on Feb. 9, 2005.

(51) Int. Cl.
C12Q 1/68 (2006.01)
C12P 19/34 (2006.01)

(52) U.S. Cl.
CPC .............. *C12Q 1/6806* (2013.01); *C12P 19/34* (2013.01); *C12Q 1/6813* (2013.01); *C12Q 1/6869* (2013.01)
USPC ........................... 435/6.1; 435/6.11; 435/6.12

(58) Field of Classification Search
None
See application file for complete search history.

(56) References Cited

U.S. PATENT DOCUMENTS

| 5,409,811 | A | 4/1995 | Tabor et al. | |
|---|---|---|---|---|
| 5,888,819 | A | 3/1999 | Goelet et al. | |
| 5,945,312 | A * | 8/1999 | Goodman et al. | 435/91.1 |
| 6,287,774 | B1 | 9/2001 | Nikiforov | |
| 6,291,164 | B1 | 9/2001 | Blakesley | |
| 6,379,940 | B2 | 4/2002 | Moffett et al. | |
| 6,399,335 | B1 | 6/2002 | Kao et al. | |
| 6,617,138 | B1 | 9/2003 | Rudi et al. | |
| 6,699,655 | B2 | 3/2004 | Nikiforov | |
| 6,764,839 | B2 | 7/2004 | Blakesley | |
| 6,917,726 | B2 | 7/2005 | Levene et al. | |
| 6,965,020 | B2 | 11/2005 | McGall et al. | |
| 7,041,812 | B2 * | 5/2006 | Kumar et al. | 536/23.1 |
| 7,056,661 | B2 | 6/2006 | Korlach et al. | |
| 7,344,835 | B2 | 3/2008 | Biakesley | |
| 7,361,466 | B2 | 4/2008 | Korlach et al. | |
| 2003/0044781 | A1 | 3/2003 | Korlach et al. | |
| 2003/0124576 | A1 | 7/2003 | Kumar et al. | |
| 2004/0110180 | A1 | 6/2004 | Recipon et al. | |
| 2004/0132155 | A1 | 7/2004 | Plowman et al. | |
| 2004/0157306 | A1 | 8/2004 | Plowman et al. | |
| 2004/0203097 | A1 | 10/2004 | Yue et al. | |
| 2006/0060766 | A1 | 3/2006 | Turner et al. | |
| 2006/0194232 | A1 | 8/2006 | Turner et al. | |
| 2007/0141598 | A1 | 6/2007 | Turner et al. | |
| 2007/0172860 | A1 | 7/2007 | Hardin et al. | |
| 2010/0317005 | A1 | 12/2010 | Hardin et al. | |

FOREIGN PATENT DOCUMENTS

| EP | 0123300 A2 | 10/1984 |
|---|---|---|
| WO | WO 9405797 A1 | 3/1994 |
| WO | 9822615 A1 | 5/1998 |
| WO | WO 0109389 A2 * | 2/2001 |

OTHER PUBLICATIONS

Inazuka et al., "One-tube post-PCR fluorescent labeling of DNA fragments," Genome Research, 1996, vol. 6, pp. 551-557.*
Blasco, M.A. et al., "Characterization and mapping the pryophosphorolytic activity of the ø29 DNA polymerase" J Biol Chem (1991) 266(12):7904-7909.
Kelman, Z. et al., "Processivity of DNA polymerases: two mechanisms, one goal" Structure (1998) 6(2):121-125.
Rozovskaya, T.A. et al., "The mechanism of prophosphorolysis of RNA by RNA polymerase" Biochem J (1984) 224:645-650.
International Search Report and Written Opinion dated Jun. 3, 2008 for related case PCT/US2006/004810.
International Preliminary Report on Patentability dated May 7, 2009 for related case PCT/US2006/004810.
Anand, R., et al. (2004) Biochemistry 43(9): 2384-2393.
Armstrong, S.R., et al. (1996) Strucure 4: 97-107.
Caradoc-Davies, T.T., et al. (2004) J. Mol. Biol. 337: 337-354.
Cherfils, J., et al. (1994) Biochemistry 33(31):9062-9069.
Cooperman (1982) "The Mechanism of Action of Yeast Inorganic Pyrophosphatase." Methods in Enzymology, 87:526-548.
Esteban-Gamboa, A., et al. (2000) J. Med. Chem. 43(5): 971-983\.
GenBank Accession No: G1:3996246, Millan, J.L., Dec. 1998 [retrieved on-line on Mar. 21, 2009, from http://www.ncbi.nlm.nih.gov/.
Kukko-Kalske and Heinonen (1985) "Inorganic Pyrophosphate and Inorganic Pyrophosphatase in *Escherichiac coli*." Int. J. Biochem, 17(5):575-580.
Kunitz (1951) "Crystalline Inorganic Pyrophosphatase Isolated from Baker's Yeast." Journal of General Physiology, 423-450.
Lahiri, S. D., et al. (2002) Biochemistry 41:13861-13867.
Ötvös, L., et al. (1987) Nuc. Ac. Res. 15 (4): 1763-1777.
PCR 2: A Practical Approach. (M.J. McPherson, B.D. Hames and G.R. Taylor eds., 1995).

(Continued)

*Primary Examiner* — Young J Kim
(74) *Attorney, Agent, or Firm* — Deana A. Arnold

(57) ABSTRACT

The present invention relates to preparation of nucleotide compositions and uses thereof for conducting nucleic acid analyzes. The compositions and methods embodied in the present invention are particularly useful for nucleic acid analyzes that require high-resolution detection of labeled nucleotides or labeled nucleic acid targets.

19 Claims, 4 Drawing Sheets

(56) References Cited

OTHER PUBLICATIONS

Quirk, Michael and Julian Serda (2001) Semiconductor Manufacturing Technology. Upper Saddle River: Prentice Hall.
Ragione, F.D., et al. (1985) Biochem. J. 232:335-341.
Ramanathan, A., et al. (2005) Analytical Chem. 337: 1-11.
Rodina et al. (2008) "Metal Cofactors Play a Dual Role in Mycobacterium Tuberculosis Inorganic Pyrophosphatase." Biochemistry 73(8):897-905.
Sambrook, J., et al. (1989) Molecular Cloning: A Laboratory Manual. 2nd Edition. New York: Cold Spring Harbor Laboratory Press.
Schramm, V.L. (2005) Archives of Biochem. And Biophysics 433: 13-26.
Teplyakov et al. (1994) "Crystal Structure of Inorganic Pyrophosphatase from *Thermus thermophilus*." Protein Science, 3:1098-1107.
Wolf, Stanley (1995) Silicon Processing for the VLSI Era. Sunset Beach: Lattice Press.
Xiao et al. (2004) "Role of Excess Inorganic Pyrophosphate in Primer-Extension Genotyping Assays." Genome Research, 14:1749-1755.
Yang et al. (2009) "DFT Study on the Mechanism of *Escherichia coli* Inorganic Pyrophosphatase." J. Phys. Chem B, 113:6505-6510.
Yano, S. et al. (2004) Bioorg. Med. Chem. 12: 3443-3450.
Yu, H., et al. (1994) Nuc. Ac. Res. 22 (15): 3226-3232.
Zhu, Z., et al. (1994) Nuc. Ac. Res. 22 (16): 3418-3422.
Zipfel, Warren R. et al. (2003) Nonlinear Magic: Multiphoton Microscopy in the Biosciences. Nature Biotechnology. 21(11): 1369-1377.
First Examiners Report dated Jan. 10, 2011 for related case AU 2006213692.

\* cited by examiner

US 8,927,211 B2

NUCLEOTIDE COMPOSITIONS AND USES THEREOF

CROSS-REFERENCE TO RELATED APPLICATIONS

This application is a divisional of U.S. patent application Ser. No. 11/352,170, filed Feb. 9, 2006, now U.S. Pat. No. 7,767,394 which claims the benefit of Provisional U.S. Patent Application No. 60/651,846, filed Feb. 9, 2005, the full disclosures of which are incorporated herein by reference in their entirety for all purposes.

INCORPORATION-BY-REFERENCE OF MATERIAL SUBMITTED BY U.S.P.T.O. eFS-WEB

The instant application contains a Sequence Listing which is being submitted in computer readable form via the United States Patent and Trademark Office eFS-WEB system, and is hereby incorporated by reference in its entirety for all purposes. The txt file submitted herewith contains only one 4 KB file (01000303.TXT).

TECHNICAL FIELD

The present invention relates to preparation of nucleotide compositions and uses thereof for biological research and diagnostic applications, e.g., in conducting nucleic add analyses. The compositions and methods embodied in the present invention are particularly useful for nucleic acid analyses that require high-resolution detection of labeled nucleotides or labeled nucleic acid targets.

BACKGROUND OF THE INVENTION

In conducting nucleic acid analyses based on recognition of differentially labeled nucleotides or nucleic targets, the purity of the labeled nucleotides or targets can be of paramount importance. While the conventional methods of labeling a nucleotide or polynucleotide and the methods for purifying these labeled molecules are well-developed, the efficiencies for both the labeling and purification techniques are less than perfect and will tend to result in compositions that are not hundred percent pure. The presence of unlabeled nucleotides or targets in sequencing or hybridization reaction mixtures, respectively, can result in high background noise signals, result in errors in base calling or in detection of a specific hybridization event, and cause other difficulties in different types of analyses. The problem of impure nucleotide compositions can be particularly exacerbated in nucleic acid analyses such as single-molecule sequencing or hybridization that require high-resolution detection of the labeled nucleotides or labeled nucleic acid targets. In case of single-molecule sequencing, the problem can stem from the tendency of many polymerase enzymes to exhibit a preference for natural nucleotides over the labeled nucleotide analogs. This preference can be as much as a hundred-fold or more, resulting in a large fraction of missed bases even for small inpurity levels in the mix.

Thus, there remains a considerable need for improved nucleotide and nucleic acid compositions particularly suited for high-resolution sequencing and hybridization assays.

SUMMARY OF THE INVENTION

The present invention relates to the preparation of labeled nucleotides or labeled target polynucleotides particularly suited for high-resolution nucleic acid analyses.

Accordingly, the present invention provides a composition comprising a mixture of labeled nucleotides or nucleotide analogs that is substantially free of unlabeled nucleotides or analogs.

The present invention also provides a composition comprising a mixture of labeled nucleic acid targets that is substantially free of unlabeled nucleic acid targets.

The present invention further provides methods of using the invention compositions for conducting nucleic acid analyses including but not limited to hybridization assays and DNA sequencing assays.

Specifically, the present invention provides a method for producing a nucleotide composition. The method involves providing a mixture containing at least one labeled nucleotide or nucleotide analog; treating the mixture with an agent that selectively renders unlabeled nucleotides or nucleotide analogs substantially incapable of participating in an analytical reaction of interest in which a labeled nucleotide or nucleotide analog participates. In one aspect, the treating step renders the unlabeled nucleotides or nucleotide analogs unincorporatable by a polymerase enzyme in a template-dependent polymerization reaction. The agent can comprise an enzyme. In some embodiments, the enzyme is selected from the group consisting of a phosphatase (e.g., shrimp alkaline phosphatase, calf intestinal phosphatase), a P-ribosyl transferase, a nucleoside deoxyribosyl transferase, a phosphorylase, a nucleosidase, a nucleoside deoxyribosyl transferase, and a polymerase. In other embodiments, the agent comprises a polymerase enzyme and divalent metal ion such as $Mg^{2+}$ or $Mn^{2+}$. Where desired, the treating step can result in less than about 10%, about 5%, about 1%, about 0.1% or even less than about 0.01% of the nucleotides or nucleotide analogs in the mixture are unlabeled nucleotides or nucleotide analogs.

The present invention also provides a method of sequencing a nucleic acid. The method involves the steps of providing a reaction mixture comprising a template nucleic acid, a primer sequence complementary to the template nucleic acid sequence, a polymerase enzyme, and a nucleotide composition comprising a labeled nucleotide or nucleotide analog and said composition being substantially free of unlabeled nucleotides or nucleotide analogs; and detecting incorporation of the labeled nucleotide or nucleotide analog by the polymerase, into a nascent nucleic acid strand. In one aspect, the providing step comprises first treating the nucleotide composition with an agent that selectively alters unlabeled nucleotides or nucleotide analogs so that they become substantially unincorporatable by the polymerase enzyme. In another aspect, the reaction mixture comprises less than about 5%, 1%, 0.1% or even less than about 0.01% of the nucleotides or nucleotide analogs are unlabeled nucleotides or nucleotide analogs. In another aspect, the reaction mixture comprises at least two different labeled nucleotides or nucleotide analogs. In yet another aspect, the reaction mixture comprises a single complex of a template nucleic acid, a polymerase enzyme, and a nascent strand that is complementary to the template nucleic acid. Where desired, the reaction mixture comprises at least four different labeled nucleotides or nucleotide analogs. In some embodiments, the detecting step is performed during incorporation of the labeled nucleotide or nucleotide analog by the polymerase into the nascent nucleic acid strand. Where needed, the detecting step involves detecting an optical signal from the labeled nucleotide or nucleotide analog. Such detection can take place during the incorporation of the labeled nucleotides or nucleotide analogs, and can involve detecting incorporation of the labeled nucleotide or nucleotide analog into the single complex. Where desired, the template nucleic acid and/or the polymerase can be immobilized to a support.

The present invention further provides a nucleic acid sequencing reaction mixture. The mixture comprises a template nucleic acid; a primer nucleic acid that is complementary to a portion of the template nucleic acid; a polymerase enzyme; a labeled nucleotide or nucleotide analog; wherein the sequencing reaction mixture is substantially free of unlabeled nucleotides or nucleotide analogs. In one aspect, the mixture comprises less than about 5% of the nucleotides or nucleotide analogs are unlabeled nucleotides or nucleotide analogs. In another aspect, the mixture comprises less than about 1%, 0.1% or even less than 0.01% of the nucleotides or nucleotide analogs are unlabeled nucleotides or nucleotide analogs. In another aspect, the mixture comprises divalent ions, including but not limited to $Mg^{2+}$ and $Mn^{2+}$. In yet another aspect, at least one of the following including polymerase, the template nucleic acid and the primer nucleic acid, is immobilized on a solid support.

The present invention also includes a method of treating a nucleic acid target. The method involves the steps of providing a nucleic acid target composition comprising at least one labeled nucleic acid target; treating the nucleic acid target composition with an agent that selectively renders unlabeled nucleic acid target substantially incapable of participating in a analytical reaction of interest in which the labeled nucleic acid target participates. In one aspect, the agent is an exonuclease enzyme that selectively digests the unlabeled nucleic acid target as compared to the labeled nucleic acid target. The exonuclease can comprise a 5' exonuclease, and the labeled nucleic acid target comprises a 5' label. In another aspect, the unlabeled nucleic acid target is rendered unable to hybridize to a nucleic acid sequence that is complementary to the labeled nucleic acid target.

Further provided herein is a method of monitoring nucleotide binding by a nucleotide binding molecule. The method comprises contacting the nucleotide binding molecule with a terminal phosphate labeled nucleotide or nucleotide analog; and detecting a level of binding of the terminal phosphate labeled nucleotide with the nucleotide binding molecule. In one aspect, the terminal phosphate labeled nucleotide or nucleotide analog is a nucleoside polyphosphate. The nucleoside polyphosphate can be selected from a nucleoside triphosphate, a nucleoside tetraphosphate, a nucleoside pentaphosphate and a nucleoside hexaphosphate. Where desired, the nucleoside polyphosphate comprises adenosine polyphosphate and any polyphosphate of any other known bases.

Also included is a method of sequencing nucleic acids, comprising the steps of locating the respective positions of a plurality of template nucleic acids in a field of immobilized polynucleotides; exposing said field to a polymerase and a nucleotide composition comprising at least one labeled nucleotide or nucleotide analog, said composition being substantially free of unlabeled nucleotides or nucleotides analogs, under conditions that allow said nucleotide to be incorporated in a primer hybridized to said template molecule if said nucleotide or nucleotide analog is complementary to a nucleotide in said template immediately 5' of said primer; determining the position or positions of optical signal emanating from label attached to a nucleotide or nucleotide analog that has been incorporated in said primer; and recording the identity and position of an incorporated nucleotide based upon said optical signal. In certain embodiments, the method further comprises the step of washing said field in order to eliminate unincorporated nucleotides. In other embodiments, the method further comprises the step of neutralizing said label after said determining step.

The present invention also provides another method of sequencing a nucleic acid. The method comprises (a) providing a complex comprising a polymerase and a target nucleic acid such that said polymerase is capable of incorporating a nucleotide complementary to a nucleotide on the target nucleic acid, wherein the complex is immobilized to a solid support; (b) providing a nucleotide composition comprising at least one labeled nucleotide or nucleotide analog to the complex to effect polymerizing a nucleotide into a nascent strand that is complementary to the target nucleic acid, wherein the nucleotide composition is substantially free of unlabeled nucleotides or nucleotides analogs; (c) optically detecting the incorporated nucleotide by sensing its detectable label, wherein said detecting is performed by passing radiation through the complex at a spatial location of the complex where said label is expected to occur; (d) repeating, with the complex immobilized on the support, steps (b) through (c) so that a plurality of nucleotides incorporated is identified and, as a result, a sequence of the target nucleic acid is determined. In some embodiments, the detecting step is effected by a technique that reduces background noise from unincorporated labeled nucleotides. In other embodiments, the incorporated nucleotide is capable of incorporating further nucleotides.

Finally, the present invention provides a method for identifying one or more nucleotides in a target nucleic acid. The method comprises (a) obtaining an array of support-bound target nucleic acids in which each of said support-bound nucleic acids is individually optically resolvable; (b) exposing said array to a polymerase, a primer capable of hybridizing to at least some of said support-bound nucleic acids and a nucleotide composition comprising at least one labeled nucleotide or nucleotide analog, said composition being substantially free of unlabeled nucleotides or nucleotides analogs, under conditions that allow said labeled nucleotide or nucleotide analog to be incorporated into said primer if said nucleotide or analog is complementary to a nucleotide in said target immediately 5' to said primer; (c) washing said array in order to remove unincorporated nucleotides or nucleotide analogs; (d) determining the presence and position of label attached to an incorporated nucleotide; (e) neutralizing any label observed in said determining step; (f) repeating steps a, b, c, and d; (g) identifying label present at any position in which presence of label has previously been determined in said determining step; (h) repeating steps a, b, c, d, and e; and (i) identifying a sequencing of nucleotides in said target nucleic acid based upon the sequence of labels detected at any given position in said array.

Various features of the nucleic acid reaction mixture and apparatus including but not limited to optical confinements disclosed herein can be used in any combinations in practicing the subject nucleic acid sequencing methods, as well as methods of monitoring nucleotide binding by a nucleotide binding molecule.

INCORPORATION BY REFERENCE

All publications and patent applications mentioned in this specification are herein incorporated by reference to the same extent as if each individual publication or patent application was specifically and individually indicated to be incorporated by reference.

DETAILED DESCRIPTION OF THE INVENTION

The practice of the present invention will employ, unless otherwise indicated, conventional techniques of Integrated Circuit (IC) processing biochemistry, chemistry, molecular biology, genomics and recombinant DNA, which are within the skill of the art. See, e.g., Stanley Wolf et al., SILICON PROCESSING FOR THE VLSI ERA, Vols 1-4 (Lattice Press); Michael Quirk et al., SEMICONDUCTOR MANUFACTURING TECHNOLOGY; Sambrook, Fritsch and Maniatis, MOLECULAR CLONING: A LABORATORY MANUAL, $2^{nd}$ edition (1989); the series METHODS IN ENZYMOLOGY (Academic Press, Inc.): PCR 2: A PRACTICAL APPROACH (M. J. MacPherson, B. D. Hames and G. R. Taylor eds. (1995).

I. General Description

Figure 1:
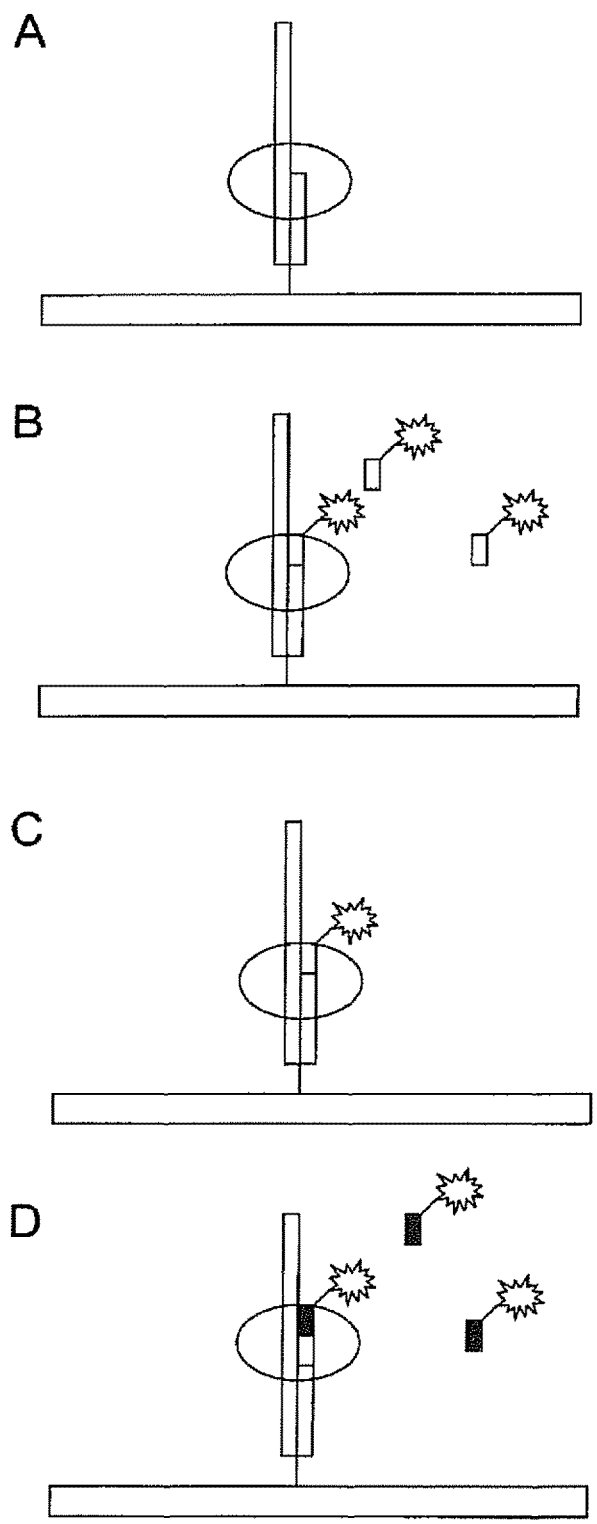
FIG. 1 schematically illustrates a single molecule sequencing by incorporation analysis using labeled nucleotides or nucleotide analogs.
Figure 2:
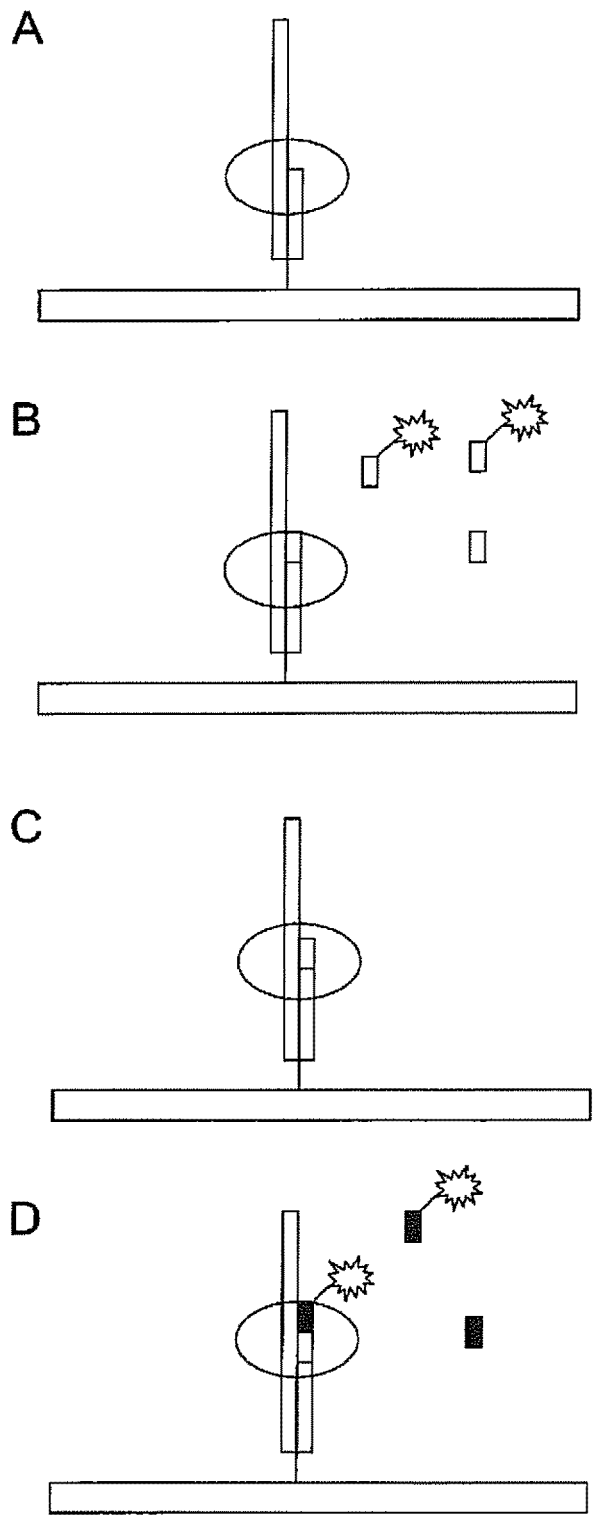
FIG. 2 schematically illustrates single molecule sequencing as shown in FIG. 1, but unlabeled nucleotides or nucleotide analogs are incorporated during the polymerization reaction.

As noted above, the present invention is generally directed to nucleotide compositions that comprise at least a first labeled nucleotide component, and in preferred aspects, 2, 3 or 4 or more different labeled nucleotide components, but which are substantially free of unlabeled nucleotides. The present invention is also directed to mixtures comprising these compositions, methods of using such compositions and systems that rely upon such compositions. As alluded to previously, the presence of unlabeled nucleotide analogs in mixture of labeled nucleotides or nucleotide analogs may cause detrimental effects on analyses or other operations that rely upon the labeled nucleotides or nucleotide analogs. Examples of such analyses include but are not limited to single molecule or complex sequencing methods that detect incorporation of individual nucleotides by a polymerase in a template dependent fashion, in order to identify the sequence of the template. FIGS. 1 and 2 schematically illustrate such a single molecule process. As shown in FIG. 1, an exemplary single molecule sequencing method employs an immobilized nucleic acid/primer/polymerase complex (Panel A). The complex may be immobilized through any of the constituent elements, e.g., through the template, through the primer or through the polymerase, and such immobilization may be direct, e.g., a covalent attachment between the immobilized constituent and the substrate, or indirect, e.g., linked via a specific or nonspecific interaction to a group that is otherwise immobilized to the substrate, e.g., directly or indirectly.

The immobilized complex is then contacted with a mixture including a labeled nucleotide or nucleotide analog, (Panel B). If the base is incorporated, the incorporation event is detected, either by washing away any unincorporated reactants and visualizing the complex (Panel C), or through methods that permit the visualization of the complex without contribution of the reactants in the background, e.g., optical confinement techniques (See, U.S. Pat. No. 6,917,726, which is incorporated herein by reference in its entirety for all purposes). Additional bases are added, step-wise to the process and their incorporation or absence of incorporation is indicative of the presence or absence of the complementary base in the template sequence at the subsequent position (Panel D).

Such sequencing methods are described in detail in published U.S. Patent Application No. 2003/0044781, the full disclosure of which is incorporated herein by reference in its entirety for all purposes. Where optical confinement techniques are used to limit observation to a limited volume including the polymerase, washing steps may not be required, and mixtures of more than one type of labeled nucleotide and potentially four or more different types of labeled nucleotides or nucleotide analogs may be added. In such cases, such optical confinement techniques render the incorporated nucleotides or nucleotide analogs distinguishable from background levels of reactants, and each type of nucleotide or nucleotide analog bears a detectably distinguishable label, thus permitting its identification and determining the template sequence.

Where the nucleotide mixture in any step includes unlabeled nucleotides or nucleotide analogs, it can lead to an increased error rate in elucidating the sequence. This potential problem is schematically illustrated in FIG. 2 with reference to the exemplary method illustrated in FIG. 1. Again, as in FIG. 1, the template/primer polymerase complex is provided immobilized upon a substrate (Panel A). A first labeled nucleotide analog is introduced to the complex. However, an unlabeled nucleotide present in this reaction mixture is incorporated by the polymerase instead of a labeled nucleotide or nucleotide analog (possibly enhanced by the preference of polymerases to native nucleotides)(Panel B). Because the incorporated base lacks a label, its incorporation is not detected, and that portion of the sequence can be misread, e.g., by determining that such base is not present at that position (Panel C). Further, subsequent incorporation events are then mischaracterized because they are shifted by the single mischaracterized base (Panel D). In particular, because the sequence is read by the addition of labeled nucleotides to the nascent strand, incorporation of an unlabeled nucleotide may cause errors in the subsequently read sequence, both in terms of the omission of the unlabeled base, and because of the improperly read positions of the ensuing bases.

As used in the specification and claims, the singular form "a", "an" and "the" include plural references unless the context clearly dictates otherwise. For example, the term "a labeled nucleotide" includes a plurality of nucleotides and mixtures thereof.

As used herein, "nucleic acid" can refer to a polymeric form of nucleotides and/or nucleotide-like molecules of any length. For example, a nucleic acid can comprise naturally occurring DNA or RNA, e.g., mRNA, or can comprise a synthetic molecule, including but not limited to cDNA and recombinant molecules generated in any manner. For example the nucleic acid can be generated from chemical synthesis, reverse transcription, DNA replication and a combination of these generating methods. The linkage between the subunits can be provided by phosphates, phosphonates, phosphoramidates, phosphorothioates, or the like, or by non-phosphate groups as are known in the art, such as peptide-type linkages utilized in peptide nucleic acids (PNAs). The linking groups can be chiral or achiral. The polynucleotides can have any three-dimensional structure, encompassing single-stranded, double-stranded, and triple helical molecules that can be, e.g., DNA, RNA, or hybrid DNA/RNA molecules.

A nucleotide can refer to a molecule comprising a base, sugar and one or more anionic groups, preferably phosphate. The molecule may comprise one, two, three, four, five or more phosphates groups and/or other groups such as sulfate. An "analog" or "nucleotide analog" (used interchangeably herein) can refer to a nucleotide-like molecule such as a structural moiety that can act substantially like a nucleotide, for example exhibiting base complementarity with one or more of the bases that occur in DNA or RNA and/or being capable of base-complementary incorporation. The terms "polynucleotide," "polynucleotide molecule," "nucleic acid molecule," "polynucleotide sequence" and "nucleic acid sequence," can be used interchangeably with "nucleic acid" herein.

A "primer" is a short polynucleotide, generally with a free 3' OH group, that binds to a target or "template" potentially present in a sample of interest by hybridizing with the target, and thereafter promoting polymerization of polynucleotide complementary to the target.

The term "hybridize" as applied to a polynucleotide refers to the ability of the polynucleotide to form a complex that is stabilized via hydrogen bonding between the bases of the nucleotide residues. The hydrogen bonding may occur by Watson Crick base pairing, Hoogstein binding, or in any other sequence specific manner. The complex may comprise two strands forming a duplex structure, three or more strands forming a multi stranded complex, a single self hybridizing strand, or any combination of these. The hybridization reaction may constitute a step in a more extensive process, such as the initiation of a PCR reaction, or the enzymatic cleavage of a polynucleotide by a ribozyme.

Hybridization can be performed under conditions of different "stringency". Relevant conditions include temperature, ionic strength, time of incubation, the presence of additional solutes in the reaction mixture, such as formamide, and the washing procedure. Higher stringency conditions are those conditions, such as higher temperature and lower sodium ion concentration, which require higher minimum complementarity between hybridizing elements for a stable hybridization complex to form. In general, a low stringency hybridization reaction is carried out at about 40° C. in 10×SSC or a solution of equivalent ionic strength/temperature. A moderate stringency hybridization is typically performed at about 50° C. in 6×SSC, and a high stringency hybridization reaction is generally performed at about 60° C. in 1×SSC.

When hybridization occurs in an antiparallel configuration between two single stranded polynucleotides, the reaction is called "annealing" and those polynucleotides are described as "complementary". A double stranded polynucleotide can be "complementary" or "homologous" to another polynucleotide, if hybridization can occur between one of the strands of the first polynucleotide and the second. "Complementarity" or "homology" (the degree that one polynucleotide is complementary with another) can be quantified in terms of the proportion of bases in opposing strands that are expected to form hydrogen bonding with each other, according to generally accepted base pairing rules.

II. Nucleotide/Nucleotide Analog Compositions of the Present Invention

As noted above, the present invention relates to compositions comprising labeled nucleotides or labeled nucleic acid targets, and their preparation, that are particularly suited for high-resolution nucleic acid analyses. Accordingly, the present invention provides a composition comprising a mixture of labeled nucleotides and/or nucleotide analogs that is substantially free of unlabeled nucleotides and/or analogs. In the context of certain preferred aspects of the invention, substantially free of unlabeled nucleotides or nucleotide analogs refers to unlabeled nucleotides or nucleotide analogs that are otherwise unable to be participants in the analysis of interest in the same fashion as the labeled nucleotides or nucleotide analogs. Specifically, the invention seeks to remove these unlabeled nucleotides or nucleotide analogs from participation in, e.g., a reaction that is being monitored using the labeled counterparts to such nucleotides. By way of example, in one aspect, the compositions to be used for, e.g., a polymerization reaction in, i.e., a sequencing by synthesis reaction, are treated so as to render the unlabeled nucleotides or nucleotide analogs un-incorporatable by a polymerase in template dependent synthesis of nucleic acids. For example, removal of a pyrophosphate group from an unlabeled nucleoside triphosphate will render the resulting monophosphate unincorporatable by a polymerase. As such, the resulting monophosphate would not be factored into a calculation of a percentage of unlabeled nucleotides for certain applications of the compositions. In the case of oligonucleotide compositions including labeled nucleic acid target sequences, treatment of the composition will typically result in the preferential digestion or other scavenging of unlabeled oligonucleotides, so that they are unavailable for subsequent hybridization analyses.

In preferred embodiments, within the mixture, less than about 30% of the nucleotides or nucleotide analogs are unlabeled, preferably less than about 20% are unlabeled, more preferably less than about 10%, still more preferably less than about 5%, more preferably less than about 1%, more preferably less than about 0.5%, or more preferably less than about 0.1% and even more preferably less than 0.01% of the nucleotides or nucleotide analogs are unlabeled nucleotides and/or unlabeled nucleotide analogs. As noted above, in certain aspects, the nucleotides and/or nucleotide analogs in question refer to those that are incorporatable by a polymerase enzyme in template-dependent polymerization reaction.

In one aspect, the composition is prepared by treating a mixture comprising labeled and unlabeled nucleotides, and/or analogs thereof, with an agent that specifically and/or preferentially modifies unlabeled or incorrectly labeled nucleotides and/or analogs to reduce their ability to be used in a hybridization, incorporation or sequencing assay. Preferably, the agent used specifically or preferentially modifies unlabeled or incorrectly labeled nucleotides and/or analogs to render them incapable of being used in a hybridization or sequencing assay.

For example, the nucleotides can be modified so that they no longer contain structures generally needed for the Watson Crick base pairing in a hybridization or template-dependent sequencing assay. In some embodiments, for example, base units of the nucleotides and/or analogs are modified. In some embodiments, phosphate groups, preferably terminal phosphate groups, of the nucleotides and/or analogs are modified to yield molecules that are incorporated to a lesser extent, or not at all, into a nascent nucleic acid strand during a template-dependent polymerization reaction. In more preferred embodiments, the terminal phosphate groups of a nucleotide and/or analogs are modified to yield molecules that cannot or that substantially cannot be incorporated into a nascent nucleic acid strand during template-dependent polymerization.

In still other embodiments, the unlabeled nucleotides are specifically or preferentially altered by incorporating them into polymeric structures, e.g., nucleic acid strands, other than in the desired template-directed synthesis or hybridization assay, e.g., they are scavenged from the composition by the agent. By "specifically or preferentially altered or modified," is generally meant that the agent displays a preferential activity toward the alteration or modification of unlabeled nucleotides or nucleotide analogs as compared to their labeled counterparts. Such preferential activity is typically at least 50% greater activity for unlabeled nucleotides or nucleotide analogs, preferably, at least 100% or two fold greater, and in still more preferred aspects is at least five, ten or more folds greater toward the unlabeled nucleotide or nucleotide analog than the labeled nucleotide or nucleotide analog. In some cases, the agent may have virtually no detectable activity toward the labeled nucleotide or nucleotide analog, e.g., any activity is below the limits of applicable detection techniques.

The agent can comprise one or more enzymes. A variety of enzymes known in the art are suitable for modifying the nucleotide or nucleotide analog as set forth herein, e.g. by cleaving or altering the configuration of the sugar, base, or phosphates, so as to disrupt the specific Watson Crick base pairing, or through its incorporation into larger, e.g., macromolecular structures such as polymers. Exemplary agents include but are not limited to guanine or adenine P-ribosyl transferase, purine nucleoside phosphorylase, AMP nucleosidase, nucleoside deoxyribosyl transferase for purines, and orotate P-ribosyl transferase, thymidine phosphorylase, thymidine or uridine nucleosidase, uridine phosphorylase, pyrimidine nucleoside phosphorylase, nucleoside deoxyribosyl transferase, polymerases, and the like.

Figure 4:
FIG. 4 illustrates the principle of preferential removal of unlabeled nucleotides from a mixture of labeled and unlabeled nucleotides by treatment with a phosphatase, and by selective polymerization by a DNA polymerase.

Enzymes applicable for modifying the terminal phosphate groups of nucleotides and/or analogs include a wide array of phosphatases. An example of such enzyme is Shrimp Alkaline Phosphatase (SAP), that removes the gamma, beta and alpha phosphates from a deoxynucleoside triphosphate (dNTP), and similarly, other nucleoside polyphosphates. The enzyme can convert specifically unlabeled dNTP into a nucleoside that is generally incapable of being utilized by a polymerase enzyme in a template-dependent sequencing reaction. It has been shown, for example, that the phosphatase activity of this enzyme is reduced or abrogated by the attachment of a blocking moiety to the terminal phosphate of an unlabeled dNTP. In a mixture of terminal phosphate-labeled and unlabeled dNTPs, the SAP will preferentially act on unlabeled dNTPs, leaving a larger proportion of labeled dNTPs available for incorporation in a polymerization and/or sequencing reaction. This is illustrated in FIG. 4. As shown, lane A of the polyacrylamide gel shown in FIG. 4 shows the result of a primer extension reaction in the absence of phosphatase treatment. In this example, a polymerase was used that cannot incorporate a labeled analog (dATP in this example) in the presence of $Mg^{2+}$. An extension product, resulting from the utilization of the presence of unlabeled dATP is apparent. Consequently, in the presence of $Mn^{2+}$ (Lane B), both the labeled nucleotide and unlabeled nucleotide are incorporated to form the primer extension product. Unlabeled dATP is essentially eliminated completely by prior treatment with shrimp alkaline phosphatase, evidenced by the lack of an polymerase-mediated extension product in the presence of $Mg^{2+}$ (Lane C). Consequently, only labeled dATP is used for the primer extension reaction in the presence of $Mn^{2+}$ (Lane D).

Other suitable phosphatases that can be used include but are not limited to calf intestinal alkaline phosphatases, and/or phosphatases of other mammals, crustaceans, and other animals. Examples of phosphatases that may be useful in the practice of the present invention can be found in US 20040203097, US 20040157306, US 20040132155; and US 20040110180.

Any other naturally occurring or synthetic phosphatases or phosphatases made by recombinant DNA technology can be used so long as they specifically or preferentially convert unlabeled nucleotides or analogs (as compared to labeled nucleotides), to molecules that are incapable of being utilized by a polymerization enzyme. Directed molecular evolution can also be used to enhance and extend the activity of related enzymes to yield the desired property described above. A wide variety of mutagenesis techniques, both in silicon and in situ, are available in the art. An example of a mutagenesis or screening assay for generating such enzymes can involve a first test for abrogation of polymerization in the system with unlabeled nucleotides, and a second screen checking for the retention of polymerization activity in the presence of labeled nucleotides. Both of these screens can be performed in the context of a highly multiplexed parallel assay. Enzymes showing some beneficial specificity can be retained, mutated by some method, and then re-screened. Methods such as these have been shown to produce many orders of magnitude improvement in specificity and performance.

Scavenging enzymes include those that will preferentially act upon the unlabeled nucleotide or nucleotide analog, relative to the labeled counterpart, in incorporating it into a resulting product, e.g., a synthesized nucleic acid polymer. For example, polymerase enzymes may be used to treat the composition in conjunction with a template strand and primer sequence, to preferentially use up any native or unlabeled nucleotide or nucleotide analogs in the mixture. Further, such polymerases may be selected based upon their relatively poor kinetic characteristics toward the labeled nucleotide or nucleotide analog, to further enhance the selection and scavenging process. A number of polymerases display the preferential incorporation activity toward unlabeled nucleotides or nucleotide analogs when supplemented by their native divalent metal ion, $Mg^{2+}$, but are less discriminating when in the presence of other divalent metal ions, e.g., $Mn^{2+}$. As such, in some cases, scavenging of unlabeled nucleotides may be carried out in the presence of $Mg^{2+}$, with application of the same polymerase to labeled nucleotides or nucleotide analogs being carried out in the presence of $Mn^{2+}$. Restated, in the case of such enzymes, transitioning from a treatment or scavenging operation to a sequencing or incorporation operation may simply involve the exchange of $Mg^{2+}$ for $Mn^{2+}$, or in some cases simple addition of $Mn^{2+}$.

A variety of polymerase enzymes useful in conjunction with the present invention are known in the art and include, e.g., Taq polymerase, an exonuclease deficient Taq polymerase, an E. coli DNA Polymerase 1, a Klenow fragment, a reverse transcriptase, a Φ29 related polymerase, a wild type Φ29 polymerase, an exonuclease deficient Φ29 polymerase, a T7 DNA Polymerase, a T5 DNA Polymerase, or any of a variety of other polymerases.

Enzymes capable of selectively or preferentially modifying a subset of unlabeled nucleotides can also be employed. For example, creatine kinase enzyme is specific for the removal of a phosphate from adenoside triphosphate, and will not act on other bases. Other enzymes that selectively or preferentially act on one or more types of unlabeled nucleotides can also be used.

The nucleotide modifying enzymes described above can be used to pre-treat the nucleotides and/or analogs, or can be used in the hybridization and/or sequencing reaction mixture, e.g., along with other hybridization or sequencing reagents.

The reaction conditions under which the modification of the nucleotides takes place will vary depending on the choice of the modifying enzymes. In one aspect, the conditions may be set within the following parameters: pH is between 4.0 and 12.0, more preferably between pH 6.0 and 10.0, more preferably between 7.0 and 9.0, more preferably less than 8, more preferably between 7 and 8, and most preferably pH 7.5 and 8.5, preferably controlled by a buffer. The buffer can be Tris-based preferably at pH 7.5 to pH 8.5. Other buffers may be used such as, but not limited to: organic buffers such as MOPS, HEPES, TRICINE, etc., or inorganic buffers such as phosphate or acetate. Buffers or other agents may be added to control the pH of the solution thereby increasing the stability of the enzymes.

Where desired, reducing agent such as but not limited to dithiotreitol (DTT) or 2-mercaptoethanol may be added to limit enzyme oxidation that might adversely affect stability of the enzymes.

In cases where some unlabeled or native nucleotides are required for the polymerization reaction, the option of using an enzyme that acts on all unlabeled nucleotides present in the reaction mix is less preferable, because the enzyme would destroy the native compounds needed for the assay. In this case, the nucleotides can be pretreated prior to mixing. In addition, the enzyme activity must be inactivated or depleted before mixing the various components together.

For example, this can be achieved by heat inactivation, e.g., SAP can be inactivated using heat in some embodiments. In some embodiments, the enzyme can be physically removed via purification of the reaction mixture, e.g., through dialysis or diafiltration, gel filtration chromatography, selective precipitation, and the like. In still other aspects, the enzyme agent may be provided upon a solid support, e.g., in a column or as a dispersion, and the treatment step would involve contacting the nucleotide composition with the solid support bound enzyme. When in column form, the column can provide a bioreactor for the treatment of nucleotide compositions that would be flowed through the column, e.g., in a continuous flow process. Alternatively, a dispersion or suspension of solid support bound enzyme may be slurried, e.g. in a batch process, with the nucleotide composition and removed by filtration, centrifugation or the like. A variety of chromatographic media and other solid phase media are commercially available to which enzymes may be readily immobilized.

In another embodiment of the invention, more than one enzyme is used in tandem to purify the mixture. For example, a nucleoside diphosphate kinase enzyme can be used in conjunction with a creatine kinase enzyme, or some other ATP utilizing system. The first enzyme will preferentially de-phosphorylate unlabeled native nucleotides over terminal phosphate labeled nucleotide analogs. The action of the diphosphate kinase is to remove one phosphate from the nucleotide, transferring it to an adenoside diphosphate, converting it to an adenoside triphosphate. The second enzyme, the ATP utilizing enzyme is present to allow recycling of the adenosine diphosphate for further purification. Multi-enzyme systems are useful generally in this and other respects. More than two enzymatic steps can be used in tandem in some embodiments. For example, three, four, five or more enzymes can be used to decrease the proportion of unlabeled nucleotides and/or unlabeled nucleotide analogs to desired low levels.

In yet another embodiment, an antibody (or aptamer) affinity purification method is used with specific selectivity for the label moiety of the nucleotide analog. The mixture is contacted to a solid support carrying said antibody or aptamer and the non-labeled molecules are eluted away from the solid support. The desired compounds are then eluted from the solid support under conditions nondestructive to the desired compound.

Upon completion of the pre-treatment, the enzymes can be heat inactivated by raising the reaction temperature to at least about ° C., preferably between about 65° C. to about 80° C. Alternatively, the enzymes can be depleted from the reaction mixture by, e.g., centrifugation through a filter (e.g., Millipore) that has a molecular weight cutoff smaller than the size of the enzyme.

The purity of the mixture of modified nucleotides can be ascertained by a variety of means available in the art. For instance, one can assay for free phosphate, e.g. with the EnzChek® Phosphate Assay Kit (Molecular Probes), or by any conventional chemical phosphate assay methods. One can also use a polymerase that does not utilize the labeled nucleotide and/or analog, and look at decrease of DNA synthesis. In this case, one can perform a time course or alkaline phosphatase titration. Alternatively, if the polymerase accepts both the labeled nucleotide and/or analog and the unmodified nucleotide, one can look at the change in the ratios with increasing or longer phosphatase treatment, given the speeds of synthesis for both are known.

In addition, the purity of a mixture can be assayed by the introduction of a nucleotide-specific enzyme or enzyme system. The products of such a reaction can be easily detected to produce a measure of purity. In one aspect, the purity is assayed by using a sulfurylase/luciferase system to detect the presence of pyrophosphate in the mixture following a reaction that converts unlabeled or native nucleotides to pyrophosphate and either NMP or nucleic acid chains. In another aspect, a polymerization reaction is performed in which the analogs are labeled with fluorophores, and fluorescence is detected upon incorporation of nucleotide. Impurities of unlabeled nucleotides are detected by the occurrence of missed bases in a known sequence. For example, if a repeating sequence of ATCG is contacted with a polymerase capable of incorporating nucleotide analogs labeled at the terminal phosphate, then in a sequencing assay (e.g., such as the one described in U.S. Ser. No. 09/572,530, now U.S. Pat. No. 7,056,661) a sequence of fluorescent pulses will be seen in the same sequence. The presence of unlabeled native nucleotides will be manifest by deletions in the sequence of pulses, e.g. ATCGATCGATGATCG (SEQ ID NO. 1), where the deletion is the "C" that should have been present at the $11^{th}$ position. Alternatively, the terminal deoxynucleotidyl transferase referred to above can be used in the presence of luciferase to detect impurities via chemiluminescence.

The present invention also provides a composition comprising a mixture of labeled nucleic acid targets that is substantially free of unlabeled nucleic acid targets. Such composition can be prepared by employing an agent that specifically modifies unlabeled nucleic acid targets. Alternatively, the mixture is prepared by synthesizing the labeled targets using a mixture of labeled nucleotides that is substantially free of unlabeled nucleotides in a polymerization reaction. In preferred embodiments, the mixture comprises less than about 30%, preferably less than about 20%, more preferably less than about 10%, more preferably less than about 5%, more preferably less than about 1%, more preferably less than about 0.5%, or more preferably less than about 0.1% and even more preferably less than 0.01% of unlabeled nucleic acid targets.

III. Uses of the Compositions of the Invention

The present invention further provides methods of using the invention compositions for conducting nucleic acid analyses including but not limited to hybridization assays and DNA sequencing assays.

Accordingly, in some embodiments, the compositions are employed in nucleic acid sequencing, e.g., sequencing by synthesis or by exploiting the exonuclease activity of certain polymerases. Such embodiments relate to a method of sequencing one or more target nucleic acid molecules. The method involves the steps of: (a) providing the target nucleic acid(s), primers complementary to the target nucleic acid(s), at least one polymerization enzyme, and a composition of the present invention, for example a composition comprising a mixture of one or more than one type of nucleotides and/or nucleotide analogs to be incorporated into nascent nucleotide strands, where the mixture is free or substantially free of unlabeled nucleotides and/or unlabeled nucleotide analogs; (b) allowing polymerization reaction to occur, e.g., subjecting (a) to conditions suitable for formation of nascent nucleotide strands by template-dependent extension of primers by the polymerization enzyme wherein labeled nucleotides and/or labeled nucleotide analogs are incorporated in the nascent strands; and (c) identifying the nucleotide incorporated or being incorporated, thereby determining the sequence of the target nucleic acid(s).

In some embodiments of the invention, a polymerase enzyme that is highly promiscuous can be used. Alternatively, an enzyme with a very active 3'-5' exonuclease activity can be use that allows the system to cycle futilely at a particular base. This reaction will consume all of the native nucleotides in the reaction mix while leaving the analogs untouched. Alternatively, a terminal deoxynucleotidyl transferase can be used in the same capacity, provided that naturally occurring or artificially engineer variants can be produced that will not accommodate nucleotide analogs of one type or another. This selectivity could extend to any type of nucleotide analog, as steric interactions may prevent non-natural substrate from being utilized. Selective preference is preferably as high as about 50%, more preferably as high as 60%, more preferably as high as about 100%, more preferably as high as about 2 or more folds.

The identity of the nucleotide incorporated or being incorporated may be determined by any of the techniques known in the art, e.g., and used in sequencing by synthesis. In preferred embodiments, the nucleotide being incorporated is determined by detecting the label released on a terminally labeled phosphate (or other anionic group). The label may be a fluorescent or fluorogenic group, such as a fluorophore, e.g., where flourophores that absorb and/or emit at different wavelengths are used to label different types of nucleotides. In some embodiments, the methods may employ multiple fluorophores as an energy transfer or FRET pair, e.g., where a donor flourophore is attached to the polymerizing agent and acceptor fluorophores are attached to terminal phosphates of nucleotides to be incorporated. Alternatively, donor and quencher fluorophores may be coupled to the same nucleotide or nucleotide analog such that incorporation of the nucleotide analog releases the quencher or donor molecule, resulting in a fluorescent signal being generated. For example coupling one member of the pair to the base or sugar moiety while the other member of the pair is coupled to the terminal phosphate group. In other embodiments, the label used may involve luminescence, chemi-luminescence, quantum dots, and/or mass labels.

In some embodiments, the compositions of the instant invention further comprise one or more nucleotides bearing a blocking moiety, e.g., a photocleavable blocking moiety. In some embodiments, the sequencing reaction is carried out on a solid and/or semi-solid support. In some embodiments, the support comprises one or more depressions, e.g., a microwell. One or more of the target, primer and/or polymerizing agent can be bound to the support, e.g., by covalent, ionic, hydrophobic and/or other bonding. In some embodiments, the composition of the instant invention further comprises one or more nucleotides bearing blocking moiety, e.g., a photocleavable blocking moiety. In some embodiments, the sequencing reaction is carried on a solid and/or semi-solid support. In some embodiments, the support comprises one or more depressions, e.g., a micro-well. One or more of the target, primer and/or polymerizing agent can be bound to the support, e.g., by covalent, ionic, hydrophobic and/or other bonding.

In particularly preferred aspects, the compositions of the invention are employed in nucleic acid sequence analyses, and particularly those analyses that determine sequence information by incorporation of labeled nucleotides or nucleotide analogs in template-dependent polymerization. Such methods typically provide a reaction mixture that includes a template nucleic acid, a primer sequence complementary to a portion of the template sequence, and a polymerase enzyme. The primer/template and/or the polymerase enzyme are provided immobilized upon a substrate to permit identification of a given incorporation event to a given reaction, as shown in FIG. 1. The immobilized complex is then contacted with one or more labeled nucleotides or nucleotide analogs, e.g., as shown in FIG. 1. Upon incorporation, the incorporated labeled nucleotide is identified by virtue of its label. The identification may be a result of the label being incorporated into the nascent strand, with background levels of unincorporated labeled nucleotides being washed from the observation region, or it may result from retention of the labeled nucleotide within a highly confined observation volume that includes the primer/template/polymerase complex. In the methods of the present invention, prior to adding the composition comprising the one or more labeled nucleotides to the primer/template/polymerase complex, the composition is treated with an agent that selectively alters or modifies unlabeled nucleotides or nucleotide analogs to yield a composition comprising one or more labeled nucleotides or nucleotide analogs, but substantially free of any unlabeled nucleotides or nucleotide analogs that would otherwise be incorporated by the polymerase enzyme into the nascent strand.

In contrast to polymerases used to scavenge unlabeled nucleotides, polymerases used in conjunction with the sequencing methods may optionally include those that are selected for enhanced activity relative to labeled nucleotides or nucleotide analogs, including, for example phi29 type polymerases, and mutant forms of such polymerases that have been modified to, for example, remove any steric hindrance to incorporation of labeled nucleotides into the active site of the enzyme, or which otherwise have such improved kinetic characteristics.

Figure 3:
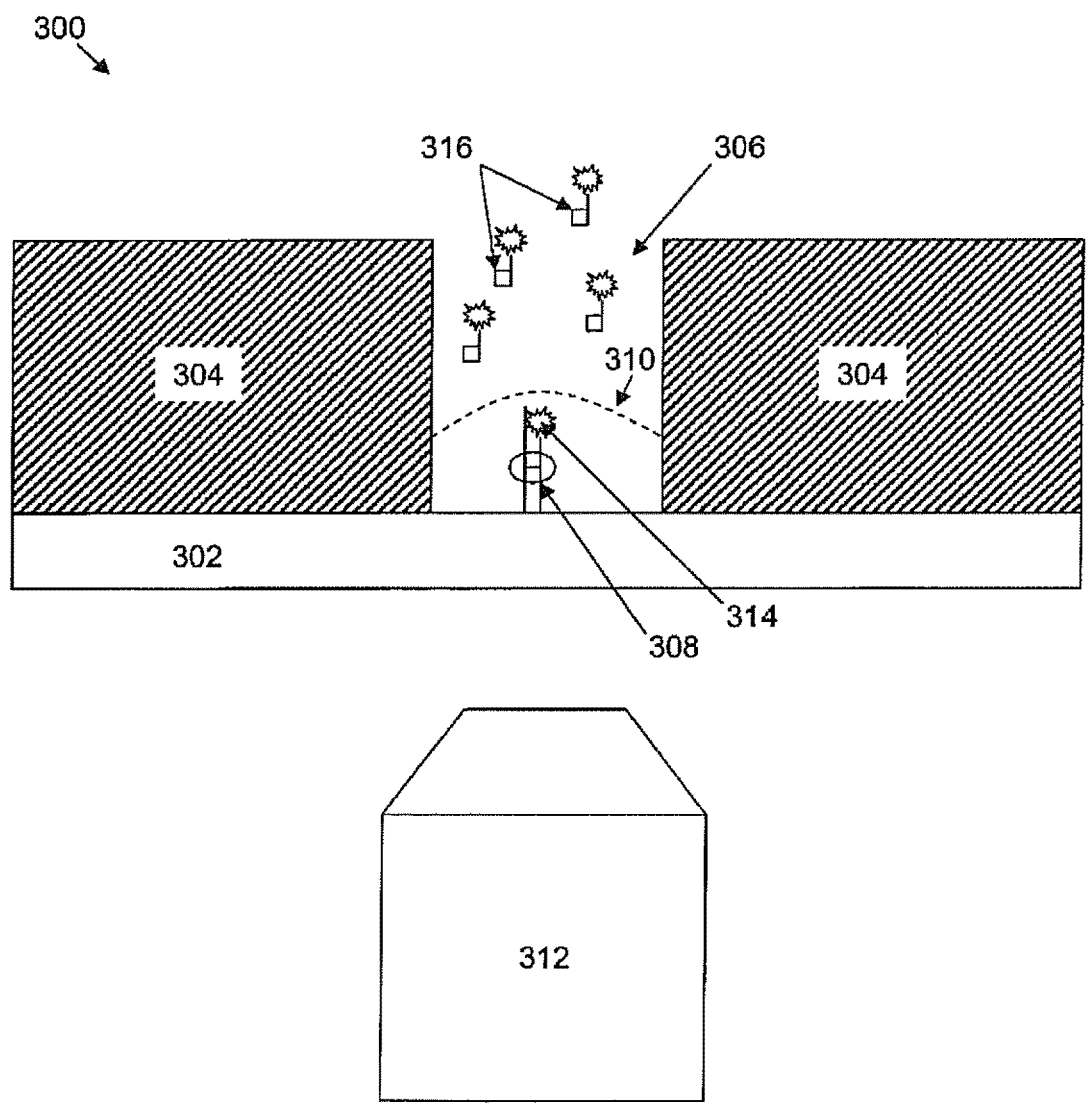
FIG. 3 schematically illustrates a zero mode waveguide used in a single molecule sequencing analysis.

As noted, where desired, the subject nucleotide mixture can be employed for single-molecule sequencing in conjunction with optical confinements, such as zero-mode waveguides. A schematic illustration of a zero mode waveguide applied to a single molecule sequencing process is shown in FIG. 3. As shown, the waveguide 300 includes the optically transparent substrate 302 over which is deposited an opaque cladding layer 304, through which the core of the zero mode waveguide 306 is disposed. The template/primer/polymerase complex 308 is provided within the core of the zero mode waveguide, and within the volume that is penetratable by excitation radiation, as indicated by dashed line 310, as dictated by the dimensions of the core 306 and the excitation radiation used. Incorporation of a labeled nucleotide 314 is detected using, e.g., a fluorescence detection system, represented by detection system 312, as the signal is occurring and remaining for some extended period, within the observation volume, while unincorporated nucleotides 316 diffuse out of the observation volume, and have only transient or no presence within the observation volume. As noted, and as will be appreciated, the illustration in FIG. 3 is intended as a schematic representation. In one aspect, the method involves the steps of (a) providing an optical confinement; (b) mixing in the waveguide—a target nucleic acid, primers complementary to the target nucleic acid, polymerization enzymes, and more than one type of nucleotides or nucleotide analogs to be incorporated into nascent nucleotide strands; (c) subjecting the mixture of step (b) to a polymerization reaction under conditions suitable for formation of the nascent nucleotide strands by template-directed/dependent extension of primers; (d) illuminating the optical confinement with an incident light beam; and (e) identifying while the template-directed/dependent extension of primer is taking place, the type of the nucleotides or the nucleotide analogs provided in step (b) being incorporated into the nascent nucleotide strands.

In one aspect, the identifying step yields a series of the nucleotides or nucleotide analogs provided in step (b) that are incorporated into the nascent nucleotide strands at consecutive base positions. In another aspect, the identifying step is effected without adjusting components of the mixture prior to reading of the next base sequence. In some preferred embodiments, the identifying step is performed under conditions that permit identifying at least 1, preferably at least about 10, more preferably at least about 100 incorporated nucleotides or nucleotide analogs per second. The target nucleic acids can be circular DNA or linear DNA, or DNA containing repeated sequences. In some embodiments, the polymerases are provided with one or more accessory proteins to modify its activity. Such accessory proteins can be a single-stranded binding protein, a primase, or helicase. Where desired, the polymerization enzyme can be processive. It should be noted that not exactly all four types of labeled nucleotides (e.g., dATP, dCTP, dGTP, dTTP) are required. Artificial nucleotide strategies can be used to re-code a strand of DNA to use only three bases, or only two, or even to use more than four. In case where all of the types present are analogs, then the modifying agent (e.g. phosphatase) can be in the mixture, but if fewer than all types are present in the mixture, and that the modifying agent used is not specific to a subset of the bases, then that agent must be abrogated or inactivated prior to mixing the reagents in the sequencing mixture to avoid deleterious removal of nucleotides.

The present invention also provides optical confinements suitable for conducting sequencing with the use of a mixture of labeled nucleotides and/or nucleotide analogs that is substantially free of unlabeled counterparts. In one aspect, the optical confinements are preferably arranged in form of an array having a surface density exceeding $4 \times 10^4$, $10^5$, $10^6$ or $10^7$ confinements per $mm^2$. In another aspect, the individual confinement pref array that provides an effective observation volume that is less than about one nanoliter ($10^{-9}$ liters), preferably on the order of zeptoliters. In certain aspects, each individual confinement provides an effective observation volume that is less than about 100 zeptoliters, or less than about 50 zeptoliters, or even less than about 10 zeptoliters. In other aspects, each of the individual confinement yields an effective observation volume that permits resolution of individual molecules present at a concentration that is higher than about one nanomolar, or higher than about 100 nanomolar, or on the order of micromolar range. In certain preferred aspects, each individual confinement yields an effective observation volume that permits resolution of individual molecules present at a physiologically relevant concentration, e.g., at a concentration higher than about 1 micromolar, higher than about 50 micromolar, or even higher than about 100 micromolar.

The array of optical confinements may comprise zero-mode waveguide or other nanoscale optical structures. Additional optical confinements suited for practicing the subject methods include field enhancement by sharp metal tips, nano-tube confinement, thin slit confinement, total internal reflection (TIR) based confinement, near-field resonant energy transfer confinement, near field aperture confinement, diffraction limited optical confinement, stimulated emission depletion confinement, and as well as all other confinements described in pending U.S. Ser. Nos. 10/944,106 and 09/572,530. The array of optical confinements may further comprise another array of confinements that does not yield the above-described effective observation volume or does not permit resolution of individual molecules. For example, the array of optical confinement can be coupled to a microtiter plate that has a comparable surface density.

The subject sequencing method can involve imaging of individual molecules confined in an optical confinement. The polymerase and/or the nucleotides are typically labeled with fluorophores that emit a distinguishable optical signal when a particular type of nucleotide is incorporated into the nascent strand. The sequence of the distinguishable signals is detected as the nucleotides are sequentially added to the nascent strand within the optical confinement. In a preferred embodiment, such detection is performed without the need to transfer, separation or washing away any reactant or by-product (e.g. fluorophore cleaved from a nucleotide) after each nucleotide addition event. In one aspect of this preferred embodiment, sequence detection is performed without adding reactants to the mixture prior to reading the next base sequence.

Imaging individual molecules confined in the subject optical confinements is performed with the aid of an optical system. Such system typically comprises at least two elements, namely an excitation source and a photon detector.

In a preferred embodiment, the excitation source is a laser, preferably a polarized laser. The choice of laser light will depend on the fluorophores attached to the different type of nucleotides and/or the polymerases. For most of the fluorescent compounds, the required excitation light is within the range of about 300 nm to about 800 nm. For proteinaceous fluorophores such as green-fluorescent protein and mutants thereof, the excitation wavelength may range from about 400 nm to about 600 nm. Those skilled in the art will know or will be able to ascertain the appropriate excitation wavelength to excite a given fluorophore by routine experimentation.

Another consideration in selecting an excitation source is the choice between one-photon and multiphoton excitation of fluorescence. Multiphoton excitation coupled with detection, also known as multiphoton microscopy ("MPM"), provides enhanced sensitivity and spatial resolution. MPM is a form of laser-scanning microscopy that uses localized nonlinear excitation to excite fluorescence within a thin raster-scanned plane. In MPM, as in conventional laser-scanning confocal microscopy, a laser is focused and raster-scanned across the sample. The image consists of a matrix of fluorescence intensity measurements made by digitizing the detector signal as the laser sweeps back and forth across the sample. Two-photon excitation probabilities are extremely small, and focusing increases the local intensity at the focal point. Although two-photon excited fluorescence is usually the primary signal source in MPM, three-photon or more excited fluorescence and second or third-harmonic generation can also be used for imaging. See, e.g., a review of multiphoton microscopy in Webb et al. *Nature Biotechnology* (2003) 21: (11) 1251-1409. A preferred MPM setup comprises MPM laser scanning microscopes and second-harmonic imaging, equipped with femtosecond mode-locked titanium sapphire lasers operating at wavelengths from 700 to 1,000 nm.

The sequence of the distinguishable signals can also be detected by other optical systems comprising elements such as optical reader, high-efficiency photon detection system, photo multiplier tube, gate sensitive FET's, nano-tube FET's, P/N diode, photodiode (e.g. avalanche photo diodes (APD)), camera, charge couple device (CCD), electron-multiplying charge-coupled device (EMCCD), intensified charge coupled device (ICCD), which may be coupled with appropriate optical components, i.e., a confocal microscope.

A preferred combination comprises wide field CCD and intensified video imaging microscopes with digital image processing capability, as well as Fluorescence Photobleaching Recovery (FPR) and Fluorescence Correlation Spectroscopy (FCS) with confocal multiphoton capability and continuous data acquisition and control. Such set up may further comprise modular instrument for quasi-elastic light scattering, laser DIC interferometry, correlation spectroscopy instrumentation, components of optical force microscopy, and Time Correlated Single Photon Counting (TCSPC). Additional applicable detection devices include scanning microscopes (e.g., scanning confocal microscopy, scanning two photon microscope).

These optical systems may also comprise optical transmission elements such as diffraction gratings, arrayed waveguide gratings (AWG), optic fibers, optical switches, mirrors, lenses (including microlens and nanolens), collimators. Other examples include optical attenuators, polarization filters (e.g., dichroic filter), wavelength filters (low-pass, band-pass, or high-pass), wave-plates, and delay lines. In some embodiments, the optical transmission element can be planar waveguides in optical communication with the arrayed optical confinements.

These and other optical components known in the art can be combined and assembled in a variety of ways to effect detection of the distinguishable signals emitted from the sequencing reaction. A preferred setup allows parallel data collection using arrays having a large number of optical confinements, where simultaneous and independent sequencing of nucleic acids takes place. In one aspect, the preferred setup can collect and process signals from more than 10, 100, 1000 or more different confinements. In certain preferred cases, these systems can collect and process signal data from as many as $10^5$ optical confinements, more than $10^6$, and even more preferably more than $10^7$ optical confinements. In another aspect, the preferred setup can monitor in real time the simultaneous and independent sequencing of nucleic acids at a speed of about 1 base per second, preferably at a speed of about 10 bases per second, more preferably at a speed of about 100 bases per second and even more preferably at 1,000 bases per second.

The present invention also provides a method of accurately assessing the ability of a nucleotide analog to be incorporated by a polymerase. In this embodiment, the analog is purified using any of the above means, and then the remaining substrate is deployed in a template-dependent synthesis reaction using a polymerase to be tested against the particular analog. The presence of synthesized DNA (as can be measured by polyacrilaminde gel electrophoresis or agarose gel electrophoresis or absorbance at 260 nm) in the mixture after the assay is then indicative of incorporation of analog. In another aspect of this embodiment, this method can be used to test if 100% of the nucleotides can be replaced with analogs satisfactorily. In this embodiment, all of the nucleotides to be used are replaced with analogs, purified by one of the above means, and then the template-directed sysnthesis assay is performed to detect synthesis.

The present invention further provides a method of conducting nucleic acid hybridization using the labeled nucleic acid compositions described herein as the targets. The method generally involves contacting the labeled nucleic acid composition with a probe and detecting for the formation of a target-probe complex. Such method finds a variety of applications including but not limited to detection of disease, identification and quantification of differential gene expression between at least two samples, linking the differentially expressed genes to a specific chromosomal location, and/or screening for compositions that upregulate or downregulate the expression or alter the pattern of expression of particular genes.

In one embodiment, the present invention provides a method of detecting differential expression of a multiplicity of gene transcripts of at least two subjects. The method involves the steps of (a) contacting a first mixture of labeled nucleic acid targets that is substantially free of unlabeled target polynucleotides corresponding to gene transcripts of a first subject with an array of polynucleotide probes under the conditions sufficient to produce stable target-probe complexes that form a first hybridization pattern; (b) contacting a second mixture of labeled target polynucleotides that correspond to gene transcripts of a second subject with an array of polynucleotide probes, under the conditions sufficient to produce stable target-probe complexes that form a second hybridization pattern; and (c) comparing the hybridization patterns, thereby detecting the differential expression of a multiplicity of gene transcripts of the subjects.

In one aspect of this embodiment, the hybridization patterns are generated on the same array. In another aspect, the hybridization patterns are generated on different arrays. In yet another aspect, the target polynucleotides are conjugated with a detectable label selected from the group consisting of an enzyme, a radioactive, and a luminescent substance. The target polynucleotides can be DNA or RNA molecules or mixtures thereof. Where desired, the target polynucleotides are cDNAs.

In still another aspect of the invention, labeled nucleotides or nucleotide analogs that include a label at a terminal phosphate group, e.g., the gamma phosphate of a triphosphate, or at the fourth, fifth or sixth phosphate of a tetra, penta or hexa phosphate, may be used as universal labeling groups for binding sites for such materials. Nucleotide binding molecules are common in biology, and the capacity to detect activity of specific binding of nucleotides to their corresponding binding sites is of great utility. For example, the function of such molecules has substantial impact on myriad biological processes, and as a result can be the focus of a great deal of pharmaceutical, diagnostic and other clinical research. Accordingly, the ability to monitor and detect the operation of such molecules, and identify potential effectors (both intra- and extramolecular effectors) of such molecules is highly valuable.

One of the most common of such active or binding sites is for adenosine triphosphate (ATP), the hydrolysis of which serves as the source of energy for a large fraction of all nonequilibrium biological reactions. As alluded to above, ATP binding sites are commonly targeted by pharmaceutical agents to modulate the effects of specific proteins. The class of protein kinases is of particular interest as drug targets. In many cases it is desirable to determine if a particular drug target's interaction with an ATP binding site is specific to that particular kinase or family of kinases.

Bioassays to determine the disposition (bound by a specific drug compound, or available for binding) have been developed which rely on the degree of binding by radiolabeled ATP. By monitoring the level of ATP binding in the presence of various test compounds, one can readily determine whether such compounds are effectors of that binding, e.g., as competitive binders with ATP, and thus, potential modulators of any downstream reactions that are dependent upon such ATP binding.

These methods are effective, but inconvenient due to the difficulties in working with radioactive materials, or in the case that nonradioactive isotopes are used, the cost and inconvenience associated with NMR or mass spectrometric methods to detect the presence of isotope-labeled ATP. Other ATP binding-site labels have been employed, but have the difficulty that they are not universally adaptable to all ATP-binding proteins.

In accordance with aspects of the present invention, terminal phosphate labeled nucleotides or nucleotide analogs, as set forth elsewhere herein, can provide an advantageous alternative to radiolabeled nucleotides. Terminal phosphate labeling has been shown in many instances to minimize the disruption in binding affinity of nucleotide binding sites to labeled nucleotides, as contrasted with labeling at the base or sugar moieties of the nucleotide (See, U.S. Pat. No. 6,399,335 and published U.S. Patent Application Nos. 2003/0044781 and 2003/0124576, the full disclosures of which are incorporated herein by reference in their entirety for all purposes). Further, such labeled nucleotides or nucleotide analogs can utilize far more convenient labeling strategies, including, e.g., fluorescent or fluorogenic labels, chemiluminescent labels, and the like. In particularly preferred aspects, fluorescent or fluorogenic labels are preferred for their ease of use and high quantum yields. Such labels may include individual fluorophores coupled to the terminal phosphate, either directly or through a linker molecule, or they may include cooperative molecules, e.g., fluorescent resonance energy transfer (FRET) pairs, and the like. A wide variety of such groups have been described previously and are readily useful for labeling such molecules (See, e.g., U.S. Pat. No. 6,399,335 and published U.S. Patent Application Nos. 2003/0044781 and 2003/0124576, previously incorporated herein).

As with other aspects of the invention, in certain preferred embodiments, the compositions and methods described herein are usefully provided as compositions of labeled nucleotides or nucleotide analogs that are substantially free of unlabeled nucleotides or nucleotide analogs.

In one embodiment of invention, a fluorescent label is attached to the terminal phosphate of an NTP molecule, and preferably an ATP molecule. Although described as ATP for ease of discussion, or generally as nucleotide triphosphates (NTPs), the molecules described herein may include only the three phosphates normally present in NTPs, or they may include additional phosphates as well as additional linker molecules in addition to the fluorophore. Further, the molecules used may include deoxy derivatives of ATP or tetra, penta- or hexaphosphate analogs. For example, where ATP binding sites are targeted, the ATP molecule may contain an OH group on the 2' carbon, or 2' deoxy nucleotides may be used.

In assay methods used to monitor ATP binding sites, one can readily take advantage of a variety of analysis formats that will provide highly multiplexed analysis opportunities and high throughput among other advantages. Such systems include, e.g., array based assay systems, microfluidic systems, bead based analysis systems, and the like. Protein arrays containing a large number of different nucleotide binding elements may be prepared as particularly effective systems, using standard protein arraying techniques, e.g., spotting processes. For example, a protein kinase array, e.g., including a wide range of different kinase enzymes or mutants, deletions, etc., of a given kinase, may be incubated with the labeled nucleotides of the invention, both in the presence and absence of a particular drug candidate compound. Incubation may be concurrent or it may involve pre-incubation with the drug candidate compound. The array is then interrogated by a means appropriate to the labeled method (for example, by an optical fluorescence scanner in the case of fluorescent labeling). The resultant signal will reflect the fraction of the molecules in the array that remained available for ATP binding (thus indicating the fraction that have bound the drug in question), and/or the degree to which such binding may have been affected. Differences in the level of binding from protein to protein will provide information about the specificity of the interaction. The dissociation constants of ATP for ATP binding sites in biomolecules varies widely, but in some cases the value can be high compared with values of other binding reactions that are typically used in microarray applications. For example, a nucleic acid hybridization interaction may have a Kd of less than a nanomolar, while a dATP binding interaction of a DNA polymerase may be in the micromolar regime. In these cases, a configuration of the array will generally be provided that allows for rapid washing and imaging of the array, as well as a high density of binding sites so as to allow multiple interactions with the substrate for each analog molecules, thus increasing the residence time on the surface. Alternatively, multiple nucleic acid moieties are attached together via linkages and include a detectable label, so that multiple simultaneous points of attachment can be established, thus increasing the stabilization of the bond with the surface in improving the retention of the labeled nucleotide through washing steps that follow the incubation with the labeled molecule.

Other solid phase assays may be employed using the same principles. For examples, immobilized ATP binding proteins may be provided, e.g., immobilized upon beads or other solid supports. The incubation steps are then followed by one or more wash steps to separate the bound from unbound labeled ATP, and the solid support is interrogated for presence or absence of bound label. Similarly, fluorescence polarization assay methods may be employed where binding of the labeled nucleotide to a large binding protein will reduce the rotational diffusion rate of the labeled nucleotide relative to its unbound state, and thus provide an indication of the level of ATP binding. This level may be compared in the presence and absence of potential drug candidate compounds, for example. Such fluorescent polarization techniques are described in, e.g., U.S. Pat. No. 6,699,655, which is incorporated herein by reference in its entirety for all purposes, and which describes the use of fluorescence polarization assay techniques in distinguishing between free and bound fluorescent compounds as a mechanism for identifying effectors of such binding in, e.g., pharmaceutical screening assays.

In conjunction with the other aspects of the invention, it is desirable in some applications that the labeled nucleotide have the greatest possible purity. In these cases, the sample may be treated either before or during incubation with a specific binder with a the agents described in substantial detail elsewhere herein, that preferentially alter or modify unlabeled nucleotides or nucleotide analogs present in the mixture so that they will not bind to the binding sites of interest, and thus create false indications of inhibition of labeled group binding by other test compounds.

In another embodiment, the present invention provides a method of detecting a polymorphism of a specific nucleotide base in a nucleic acid target. The method involves the use of a mixture of labeled nucleic acid targets that is substantially free of unlabeled nucleic acids as reactants in a single base primer extension reaction assay. As will be appreciated, extension of the primer by one base that includes a polymorphic variant will enable one to identify that polymorphic variant by virtue of incorporation of a labeled nucleotide. The presence of unlabeled nucleotides in the mixture would lead to an increased likelihood that the polymorphic variant would be mischaracterized, e.g., as being the native or mutant allele, depending upon whether the fluorescent nucleotide or nucleotide analog was targeted to be complementary to the wild type or mutant allele. Primer extension assays for single nucleotide polymorphism detection are described in, e.g., U.S. Pat. No. 5,888,819, which is incorporated herein by reference in its entirety for all purposes. As such, the use of the compositions of the invention in such assays provides enhanced accuracy to the methods.

Although described in some detail for purposes of illustration, it will be readily appreciated that a number of variations known or appreciated by those of skill in the art may be practiced within the scope of present invention. To the extent not already expressly incorporated herein, all published references and patent documents referred to in this disclosure are incorporated herein by reference in their entirety for all purposes.

What is claimed is:

1. A method for producing a nucleotide composition, comprising:
    providing a solution containing at least one labeled nucleotide or nucleotide analog, wherein the labeled nucleotide or nucleotide analog emits a detectable optical signal;
    treating the solution with an agent that selectively renders unlabeled nucleotides or nucleotide analogs substantially incapable of participating in an analytical reaction of interest in which the labeled nucleotide or nucleotide analog participates, wherein the agent displays preferential activity toward alteration or modification of the unlabeled nucleotides or nucleotide analogs as compared to the labeled nucleotide or nucleotide analog; and
    subsequent to said treating, performing an additional step of adding said solution to a reaction mixture for the analytical reaction of interest, wherein the reaction mixture comprises a primer, a template nucleic acid, and a polymerase.

2. The method of claim 1, wherein the treating step renders the unlabeled nucleotides or nucleotide analogs unincorporatable by a polymerase enzyme in a template-dependent polymerization reaction, wherein an unincorporatable unlabeled nucleotide or nucleotide analog so rendered is no longer available for incorporation into a nascent strand in the template-dependent polymerization reaction.

3. The method of claim 1, wherein the agent comprises an enzyme.

4. The method of claim 3, wherein the enzyme selectively alters the unlabeled nucleotide or nucleotide analogs via a hydrolysis, transferase, phosphorylase, or polymerase reaction.

5. The method of claim 3, wherein the enzyme comprises a polymerase that selectively scavenges unlabeled nucleotides or nucleotide analogs.

6. The method of claim 3, wherein the agent comprises a polymerase enzyme and $Mg^{2+}$.

7. The method of claim 3, wherein the enzyme comprises a phosphatase.

8. The method of claim 7, wherein the phosphatase comprises shrimp alkaline phosphatase.

9. The method of claim 7, wherein the phosphatase comprises a calf intestinal phosphatase.

10. The method of claim 1, wherein following the treating step, less than 10% of the nucleotides or nucleotide analogs in the solution are unlabeled nucleotides or nucleotide analogs that are capable of participating in an analytical reaction of interest in which a labeled nucleotide or nucleotide analog participates.

11. The method of claim 1, wherein following the treating step, less than 5% of the nucleotides or nucleotide analogs in the solution are unlabeled nucleotides or nucleotide analogs that are capable of participating in an analytical reaction of interest in which a labeled nucleotide or nucleotide analog participates.

12. The method of claim 1, wherein following the treating step, less than 1% of the nucleotides or nucleotide analogs in the solution are unlabeled nucleotides or nucleotide analogs that are capable of participating in an analytical reaction of interest in which a labeled nucleotide or nucleotide analog participates.

13. The method of claim 1, wherein following the treating step, less than 0.1% of the nucleotides or nucleotide analogs in the solution are unlabeled nucleotides or nucleotide analogs that are capable of participating in an analytical reaction of interest in which a labeled nucleotide or nucleotide analog participates.

14. The method of claim 1, wherein following the treating step, less than 0.01% of the nucleotides or nucleotide analogs in the solution are unlabeled nucleotides or nucleotide analogs that are capable of participating in an analytical reaction of interest in which a labeled nucleotide or nucleotide analog participates.

15. The method of claim 1, wherein the analytical reaction of interest is a sequencing reaction.

16. The method of claim 1, wherein the solution comprises at least two different labeled nucleotides or nucleotide analogs.

17. The method of claim 1, wherein the solution comprises at least four different labeled nucleotides or nucleotide analogs.

18. The method of claim 1, wherein the at least one labeled nucleotide or nucleotide analog comprises a nucleoside tetraphosphate, a nucleoside pentaphosphate, or a nucleoside hexaphosphate.

19. The method of claim 1, wherein at least one of the polymerase and the template nucleic acid is immobilized to a solid support.

* * * * *

SEQUENCE LISTING

<160> NUMBER OF SEQ ID NOS: 1

<210> SEQ ID NO 1
<211> LENGTH: 15
<212> TYPE: DNA
<213> ORGANISM: Artificial Sequence
<220> FEATURE:
<223> OTHER INFORMATION: An example of a read with a missing base

<400> SEQUENCE: 1
atcgatcgat gatcg                                                    15